US010568281B2

(12) United States Patent
Shin et al.

(10) Patent No.: US 10,568,281 B2
(45) Date of Patent: Feb. 25, 2020

(54) PRETREATMENT METHOD FOR DIRECTLY SEEDING IN VITRO MICROTUBER

(71) Applicant: E GREEN GLOBAL CO., LTD., Gunpo-si (KR)

(72) Inventors: Keejoon Shin, Seoul (KR); Eunyoung Jeon, Seoul (KR); Euna Seol, Ansan-si (KR); Jiyoung Park, Anyang-si (KR); Dongkeun Lee, Wonju-si (KR)

(73) Assignee: E GREEN GLOBAL CO., LTD., Gunpo-si (KR)

( * ) Notice: Subject to any disclaimer, the term of this patent is extended or adjusted under 35 U.S.C. 154(b) by 93 days.

(21) Appl. No.: 15/714,336

(22) Filed: Sep. 25, 2017

(65) Prior Publication Data

US 2018/0092317 A1 Apr. 5, 2018

(30) Foreign Application Priority Data

Sep. 30, 2016 (KR) .................. 10-2016-0126311

(51) Int. Cl.
*A01H 4/00* (2006.01)
*A01H 3/02* (2006.01)
*A01H 3/00* (2006.01)

(52) U.S. Cl.
CPC ............... *A01H 4/005* (2013.01); *A01H 3/00* (2013.01); *A01H 3/02* (2013.01)

(58) Field of Classification Search
None
See application file for complete search history.

(56) References Cited

FOREIGN PATENT DOCUMENTS

| CN | 103392595 | * | 11/2013 |
|---|---|---|---|
| JP | 2016167994 | | 9/2016 |
| KR | 19980075769 | | 11/1998 |
| KR | 20140094042 | | 7/2014 |

OTHER PUBLICATIONS

Naik et al (Micropropagation for Production of Quality Potato Seed in Asia-Pacific. Asia-Pacific Consortium on Agricultural Biotechnology, 1-45, 2007) (Year: 2007).*
Olsen et al (Efficacy of Chlorine Dioxide for Disease Control on Stored Potatoes, Amer J of Potato Res. 80:387-395, 2003) (Year: 2003).*
Coleman et al (Potato Microtubers as Research Tools: A Review. Amer J of Potato Res. 78:47-55, 2001) (Year: 2001).*
DuPont_Tyvek_Users_Manual (published 2003) (Year: 2003).*
Wrobel et al (Assessment of Possibilities of Microtuber and in vitro Plantlet Seed Multiplication in Field Conditions. Part 1: PVY, PVM and PLRV Spreading. Am. J. Potato Res. 91:554-565, 2014). (Year: 2014).*
Dieme et al (Environmental, morphological and physiological factors analyzes for optimization of potato (*Solanum tuberosum* L.) microtuber in vitro germination. Advances in Bioscience and Biotechnology, 4, 986-992, 2013) (Year: 2013).*
Mani et al (Physiology of Potato Sprouting. Journal of new sciences. Agriculture and Biotechnology, 17: 591-602, 2015) (Year: 2015).*
Sharabash (Radiation induced variation in potato for tolerance to salinity using tissue culture technique, in vitro techniques for selection of radiation induced mutations adapted to adverse environmental conditions, Proceedings of a final Research Co-ordination Meeting, 83-87, 2001). (Year: 2001).*
Macwan (In vitro multiplication and microtuber production in Potato (*Solanum tuberosum* L.), 2013) (Year: 2013).*
Korean Office Action—Korean Application No. 10-2016-0126311 dated Nov. 21, 2017, citing Nongsaro, KR 10-2014-0094042 and JP 2016-167994.
Production of In Vitro Microtubers, http://www.nongsaro.go.kr/portal/ps/psb/psbk/kidoContentsFileView.ps?kidofcomdtyNo=14540, Nongsaro Homepage.

* cited by examiner

*Primary Examiner* — Medina A Ibrahim
*Assistant Examiner* — Wayne Zhong
(74) *Attorney, Agent, or Firm* — Cantor Colburn LLP

(57) ABSTRACT

Provided is a pretreatment method for directly seeding an in vitro microtuber in an open field including: sterilizing a washed in vitro microtuber with chlorine dioxide and drying the sterilized in vitro microtuber; irradiating the dried in vitro microtuber with light and greening the dried in vitro microtuber; putting the greened in vitro microtuber in a storage container and storing the greened in vitro microtuber in a temperature range of 2 to 4° C.; and germinating the in vitro microtuber. The in vitro microtuber can quickly adapt to environment when directly seeded on a field, an early-stage management of the in vitro microtuber is facilitated, and physiological functions thereof such as vitamin synthesis is activated.

4 Claims, 3 Drawing Sheets

PRETREATMENT METHOD FOR DIRECTLY SEEDING IN VITRO MICROTUBER

CROSS-REFERENCE TO RELATED PATENT APPLICATION

This U.S. non-provisional patent application claims priority under 35 U.S.C. § 119 of Korean Patent Application No. 10-2016-0126311 filed on Sep. 30, 2016 in the Korean Patent Office, the entire contents of which are hereby incorporated by reference.

BACKGROUND

1. Technical Field

The present invention relates to a pretreatment method for directly seeding an in vitro microtuber.

2. Description of the Related Art

Potatoes can be reproduced using true seeds or vegetative reproduction, and generally, a method using vegetative reproduction is mainly used. When producing potatoes using vegetative reproduction, it is important to sow and grow virus-free high-quality seed potatoes. Therefore, certified seed potatoes being supplied to farms should be virus-free and healthy. For this, a method in which virus-free tissue culture plants obtained by growing point culture are mass-propagated to produce an in vitro microtuber (microtuber), a nutri-solution minituber (nutrition film technique (NFT)), and a stem-cutting minituber is known.

Among them, the nutri-solution minituber (NFT) can obtain large-size seed potatoes compared to the in vitro microtuber but has problems in that facilities such as a greenhouse and a vinyl house, a nutri-solution supply system, a growing bed, and the like are required, there may be great damage in entire cultivation when the nutri-solution is polluted or outage occurs, and productivity changes in accordance with seasons, regions, and species. Despite having low production cost and being convenient, the stem-cutting minituber has low productivity and is highly likely to be infected with pathogens in accordance with cleanliness of work tools when securing a stem. Also, like the nutri-solution minituber, the stem-cutting minituber has problems in that facilities such as a greenhouse are required and productivity changes in accordance with seasons and regions.

The in vitro microtuber (microtuber) has advantages of being capable of producing completely virus-free and healthy seed potatoes by being produced in tissue cultures in a sterilized container and being capable of year-round production in a limited space. Due to the advantages, a large amount of top-quality seed potatoes can be produced within a short period, and supply of high-quality potatoes is possible by significantly reducing proliferation steps from conventional 6 to 7 steps to 2 to 3 steps and reducing exposure to pathogens such as viruses that may be generated from the soil.

However, generally, due to having a very small size less than 1 g, the in vitro microtuber (microtuber) cannot be directly seeded on a field, and a method of propagating in a tray and planting on a permanent field or a method of planting in a pot and securing a mini-sized tuber is used, and a method of directly seeding on the field is not used.

However, the method of propagating in a tray and planting on a permanent field or planting in a pot and securing a mini-sized tuber involves cumbersome processes, and the method not only requires great effort but has a problem of being disadvantageous in terms of economic feasibility due to high labor cost and the like. Therefore, as a result to solve the above problems, the present inventors have completed a pretreatment method for an in vitro microtuber capable of increasing adaptability to environment of the in vitro microtuber when directly seeded on a field and facilitating an early-stage management of the in vitro microtuber.

RELATED ART DOCUMENT

Patent Document (Patent Document 1)
Korean Patent Registration No. 10-0220088 (Sep. 1, 1999)

SUMMARY

The present invention is directed to providing a pretreatment method for an in vitro microtuber capable of increasing adaptability to environment of the in vitro microtuber when the in vitro microtuber is directly seeded on a field and facilitating an early-stage management of the in vitro microtuber.

To achieve the above-mentioned object, an aspect of the present invention provides a pretreatment method for directly seeding an in vitro microtuber including a) sterilizing a washed in vitro microtuber with chlorine dioxide ($ClO_2$) and drying the sterilized in vitro microtuber; b) irradiating the dried in vitro microtuber with light and greening the dried in vitro microtuber; c) putting the greened in vitro microtuber in a storage container and storing the greened in vitro microtuber in a temperature range of 2 to 4° C.; and d) germinating the in vitro microtuber.

BRIEF DESCRIPTION OF DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EMBODIMENTS

Figure 1:
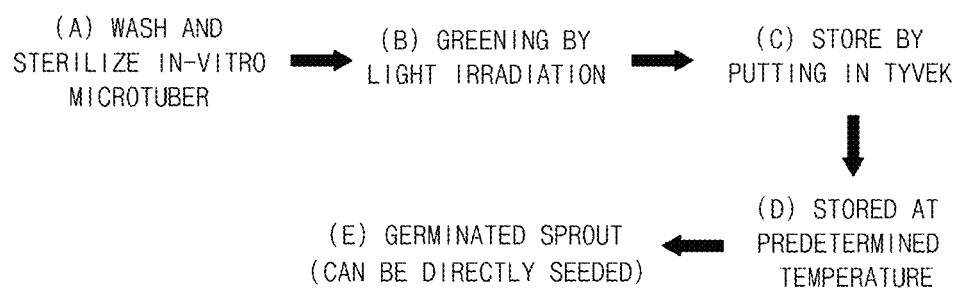
FIG. 1 illustrates the processes that respectively show steps of a pretreatment method according to an example of the present invention in order.

Hereinafter, exemplary embodiments of the present invention will be described. Although the present invention will be described with reference to embodiments, the description is merely an example, and the technical idea of the present invention and key elements and actions thereof are not limited by the description.

"Number per share" and "weight per share," which are terms used in the specification of the present invention, indicate ways of showing the number and weight on the basis of the number of plants and should be understood as the number and weight of potatoes produced from a single potato plant.

According to an example of the present invention, a pretreatment method for directly seeding an in vitro microtuber includes: a) sterilizing a washed in vitro microtuber with chlorine dioxide ($ClO_2$) and drying the sterilized in vitro microtuber; b) irradiating the dried in vitro microtuber with light and greening the dried in vitro microtuber; c) putting the greened in vitro microtuber in a storage container and storing the greened in vitro microtuber in a temperature range of 2 to 4° C.; and d) germinating the in vitro microtuber.

First, a washed in vitro microtuber is sterilized with $ClO_2$ and dried (Step a).

Generally, the in vitro microtuber (microtuber) refers to a bean-size tuber produced from a potato stem propagated in vitro, and the in vitro microtuber used in the present invention is not particularly limited as long as the in vitro microtuber is produced by the method generally used in the art.

For example, the in vitro microtuber may be obtained by collecting growing points of potatoes and culturing the growing points to acquire a basic stem, culturing the basic stem to acquire a propagated stem, and then culturing the propagated stem under specific conditions to produce a tuber.

The in vitro microtuber used in the present invention may be an in vitro microtuber from which a medium on the in vitro microtuber is completely removed by washing the in vitro microtuber with clean water one or more times, more specifically, three or more times.

In Step a, the in vitro microtuber goes through a process of sterilization by using $ClO_2$. Specifically, the process may involve dipping of the in vitro microtuber in 5 to 15 ppm of $ClO_2$ for about 10 to 20 minutes for sterilization. After the sterilization process is finished, the in vitro microtuber is dried. During this procedure, the in vitro microtuber should not be rinsed with water and is preferably dried without change after being sterilized using $ClO_2$. When being dried without change after being sterilized as above, it is easy to protect the in vitro microtuber from bacteria or such molds during storage of the in vitro microtuber.

Next, the dried in vitro microtuber is irradiated with light and greened (Step b).

Generally, color of potato skin changes to green (greening) due to photosynthesis when potatoes receive light. Particularly, by going through the light irradiation process of Step b, a tender tissue of the in vitro microtuber produced in vitro may be stiffened, and internal stability of the in vitro microtuber is improved such that spoilage or infection of pathogens is prevented.

In the example of the present invention, the process of irradiating the in vitro microtuber with light in Step b may be, specifically, performed for 7 to 10 days under conditions including 3,000 to 4,000 lux of light and 40 to 60% of humidity. Further, in the example of the present invention, the process of irradiating the in vitro microtuber with light in Step b may be, specifically, irradiating the in vitro microtuber with light for 12 hours and shading the in vitro microtuber from light for 12 hours in 24 hours of a day.

Due to characteristics thereof, the in vitro microtuber requires a germination period and needs to be carefully treated so that the in vitro microtuber is not stressed by the external environment during the entire germination period, which lasts for a month. When being greened under the above conditions, tender skin of the in vitro microtuber is most effectively stiffened right after being harvested, and in this way, the in vitro microtuber can be protected from stress due to external environment.

When irradiating the in vitro microtuber with light, if the humidity deviates from the range of 40 to 60% such that it is too humid or too dry, there are problems in that molds may be generated in the in vitro microtuber or the in vitro microtuber may be dried and withered.

When irradiating the in vitro microtuber with light, it is preferable that the in vitro microtuber be mixed frequently in order to evenly distribute light throughout the in vitro microtuber.

Next, the greened in vitro microtuber is put in a storage container and stored therein at a temperature range of 2 to 4° C. (Step c).

In the example of the present invention, a tyvek pouch may be used as the storage container. The tyvek pouch may be manufactured with a material capable of preventing an external polluting agent from entering the pouch and facilitating circulation of air in and out of the pouch.

Since a sowing period is different for each region for potatoes, after seed potatoes are harvested, the harvested seed potatoes are stored for a predetermined period, until they are taken out of the storage corresponding to the sowing period. Particularly, a flexible storage period and management of the in vitro microtuber that is harvested year-round every day are very important. In a normal storage, normal potatoes can be stored for about 5 months, and the in vitro microtuber can be stored for about 8 months. However, the in vitro microtuber that has gone through the steps of the present invention can be stored for a longer period to about 12 to 14 months.

The storage temperature is preferably maintained at a range of 2 to 4° C. This is because, in this temperature range, the rate of respiration is minimized to achieve the maximum dormancy period, ultimately, increasing the shelf life. The storage step may be performed before release corresponding to a sowing schedule.

Lastly, the stored in vitro microtuber is released corresponding to the sowing schedule and germinated (Step d).

In the example of the present invention, Step d may be performed for 4 weeks under conditions including 3,000 to 4,000 lux of light and 40 to 60% of humidity. For example, Step d may be divided into a total of 4 steps with a week as a unit.

More specifically, in the example of the present invention, Step d may include Step d1 of shading the in vitro microtuber from light for 24 hours a day for a week while sequentially changing temperatures; Step d2 of irradiating the in vitro microtuber, gone through Step d1, with light for 7 to 12 hours and shading the in vitro microtuber from light for 12 to 17 hours every day for a week; Step d3 of irradiating the in vitro microtuber, gone through Step d2, with light for 15 to 20 hours and shading the in vitro microtuber from light for 4 to 9 hours every day for a week; and Step d4 of irradiating the in vitro microtuber, gone through Step d3, with light for 20 hours and shading the in vitro microtuber from light for 4 hours every day for a week.

First, in the example of the present invention, Step d1 may be performed by shading the in vitro microtuber from light for 24 hours a day for a week while sequentially changing temperatures. More specifically, during a week in which Step d1 is performed, Step d1 may be performed at 10° C. on the first day, 15° C. on the second day, and in a temperature range of 20 to 25° C. from the third to the last day (the seventh day). Because sudden temperature change is not beneficial for physiological functions of potatoes, the temperature is preferably to be changed sequentially as above mentioned.

Next, irradiating the in vitro microtuber, gone through Step d1, with light for 7 to 12 hours and shading the in vitro microtuber from light for 12 to 17 hours every day for a week (Step d2); irradiating the in vitro microtuber, gone through Step d2, with light for 15 to 20 hours and shading the in vitro microtuber from light for 4 to 9 hours every day for a week (Step d3); and irradiating the in vitro microtuber, gone through Step d3, with light for 20 hours and shading the in vitro microtuber from light for 4 hours every day for a week (Step d4) are provided.

In the example of the present invention, Steps d2 to d4 may be performed in the temperature range of 20 to 25° C., and the temperature range is set to correspond to optimal germination conditions.

The germination step allows germination to start quickly by sufficiently shading at an early stage and accelerates photosynthesis by gradually increasing light irradiation time. The process allows a germinated sprout to grow healthily without overgrowth.

A sprout is grown from the in vitro microtuber obtained by the above pretreatment, and as a result, the in vitro microtuber has a sprout of 0.5 to 3 cm length.

As described above, the in vitro microtuber pretreated according to the present invention can quickly adapt to the environment when directly seeded on a field, an early-stage management of the in vitro microtuber is facilitated, and physiological functions thereof such as vitamin synthesis is activated. Furthermore, the in vitro microtuber which is pretreated according to the present invention has a sprout that is thicker and healthier compared to when normally treated with diffused light and has a large amount of root primordia such that a root grows out quickly when sown and the sprout quickly emerge above the ground.

Hereinafter, configuration and actions of the present invention will be described in more detail through exemplary embodiments of the present invention. However, the description below is merely an exemplary embodiment, the present invention should not be limitingly interpreted thereby in any meaning. Contents not described herein are those that can be sufficiently inferred by one of ordinary skill in the art, and description thereof will be omitted.

EXAMPLE

An in vitro microtuber produced by tissues culturing in a virus-free environment was carefully washed with running water and then dipped in $ClO_2$ for about 15 minutes for sterilization. After drying the sterilized in vitro microtuber at room temperature, the dried in vitro microtuber has undergone greening for 7 days under conditions of about 3,500 lux of light and about 55% of humidity.

The in vitro microtuber gone through the greening process was put in a tyvek pouch, which then was stored in a storage for 6 months. The stored in vitro microtuber was taken out from the storage after dormancy, a month before sowing. Specifically, a germination environment was maintained and managed under conditions of 3,500 lux of light, a temperature of 20 to 25° C., and 40 to 60% of humidity.

Specifically, the germination step was performed as follows.

First, the in vitro microtuber was shaded from light while sequentially changing temperatures for a week (the first day: 10° C., the second day: 15° C., and from the third to the last day: 20 to 25° C.), was irradiated with light for 10 hours and shaded from light for 14 hours for a week, was irradiated with light for 16 hours and shaded from light for 8 hours for a week, and, lastly, was irradiated with light for 20 hours and shaded from light for 4 hours for a week.

Comparative Example 1

Conditions were the same as in the above example except frequency of light irradiation and shading, humidity and temperature.

The germination step of Comparative Example 1 was performed as follows.

Firstly, the in vitro microtuber was shaded from light while sequentially changing temperatures for a week (the first day: 10° C., the second day: 15° C., and from the third to the last day: 20 to 25° C.), then irradiated with light for 14 hours and shaded from light for 10 hours for another week, after that irradiated again with light for 12 hours and shaded from light for 12 hours in the week after, and finally irradiated with light for 4 hours and shaded from light for 20 hours in the fourth week.

Comparative Example 2

Conditions were the same as in the above example except that sterilizing with $ClO_2$ during the pretreatment was not performed, and the in vitro microtuber was stored in a plastic container instead of a tyvek pouch.

Comparative Example 3

Conditions were the same as in the above example except that the germination process (germination step) was not performed.

Experiment

The in vitro microtuber pretreated according to the example and Comparative Examples 1 to 3 above was directly seeded (sown) on the ground, and seed potatoes were harvested after 110 days. The sowing method was the same as that of normal seed potatoes, but a distance between shares (sowing interval) and a sowing depth were slightly different in consideration of a difference in size from normal seed potatoes. Specifically, the distance between shares (sowing interval) was 20 cm, which is slightly narrower than 25 to 30 cm, which is a distance between shares (sowing interval) of normal seed potatoes, and the sowing depth was 15 cm in consideration of the size of the in vitro microtuber. Furthermore, the seed potatoes of the present invention were treated with fertilizers and chemicals throughout the whole growing period in accordance with normal seed potato cultivation practices. The experiment was conducted three times, each consisting of 50 shares for each process, and Table 1 below shows average values of the experiment repeatedly conducted three times.

TABLE 1

| Type | Loss during germination (%) | Emergence period (day) | Emergence rate (%) | Number per share (number) | Weight per share (g) | Distribution per size (%) | | | | | | Exposure to pathogens |
|---|---|---|---|---|---|---|---|---|---|---|---|---|
| | | | | | | 10 g or less | 11-50 g | 51-80 g | 81-120 g | 121-250 g | 251 g or more | |
| Example | 0 | 5 | 100 | 17.7 | 2.079 | 9 | 21 | 22 | 28 | 15 | 5 | No |
| Comparative Example 1 | 2 | 3 | 100 | 15.9 | 1.581 | 18 | 26 | 27 | 18 | 8 | 3 | No |
| Comparative Example 2 | 47 | 5 | 91 | 14.8 | 1.427 | 17 | 21 | 29 | 22 | 10 | 1 | No |
| Comparative Example 3 | 0 | 15 | 64 | 10.8 | 1.019 | 23 | 27 | 22 | 19 | 9 | 0 | No |

Other Experimental Results and Conditions

Example

Undergone the pretreatment steps of the present invention (a length of sprout was about 1 cm after the germination step)

Comparative Example 1

Conditions of the germination step were changed during the pretreatment process (a length of sprout was about 4 cm after the germination step)

Comparative Example 2

During the pretreatment process, sterilizing with $ClO_2$ and putting in a tyvek pouch were not performed (a length of sprout was about 1 cm after the germination step)

Comparative Example 3

From the pretreatment process, the germination process was not performed (a length of sprout was about 0 cm after the germination step)

Figure 3:
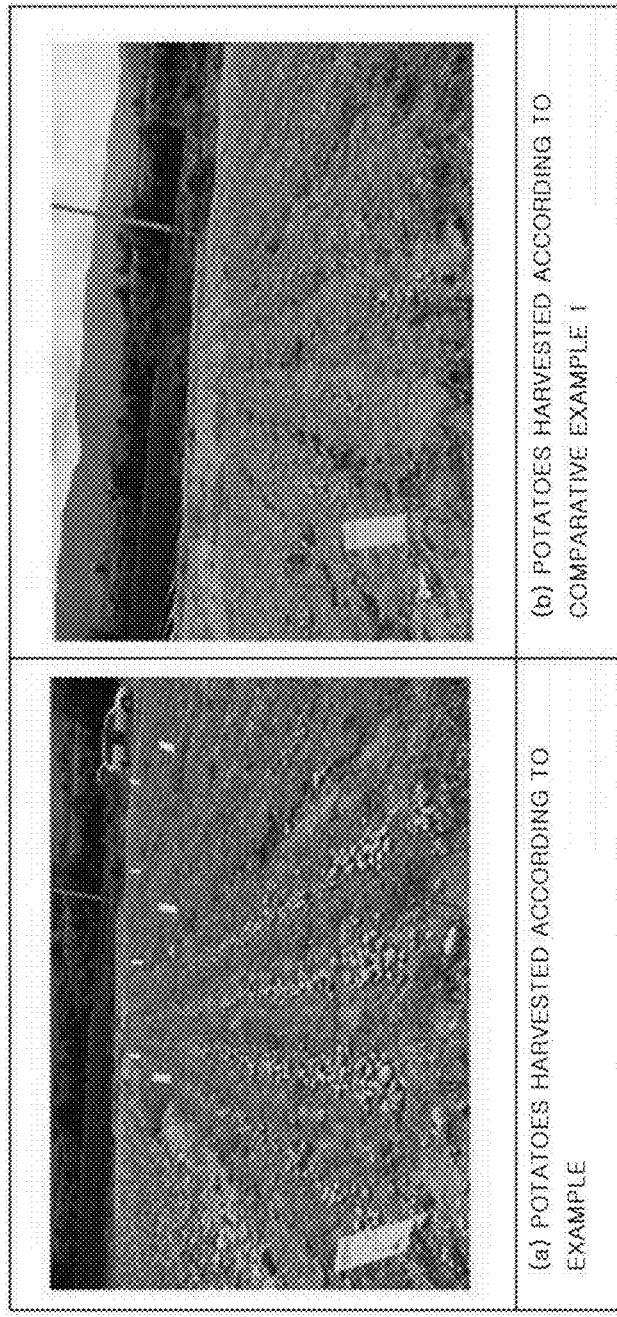
FIG. 3 illustrates pictures showing seed potatoes harvested by directly seeding and growing the in vitro microtuber according to the example and Comparative Example 1 of the present invention.

Referring to Table 1 above, Comparative Example 1 showed a similar result with the example in terms of quantity of harvested potatoes, but an average weight per share was about 500 g smaller compared to the example. This is, because Comparative Example 1 had a relatively longer sprout length, the emergence period was relatively shorter compared to the example. Also, although the number of tubers formed underground increased compared to the example, the number of small-size potatoes also increased (see (a) and (b) of FIG. 3).

Figure 2:
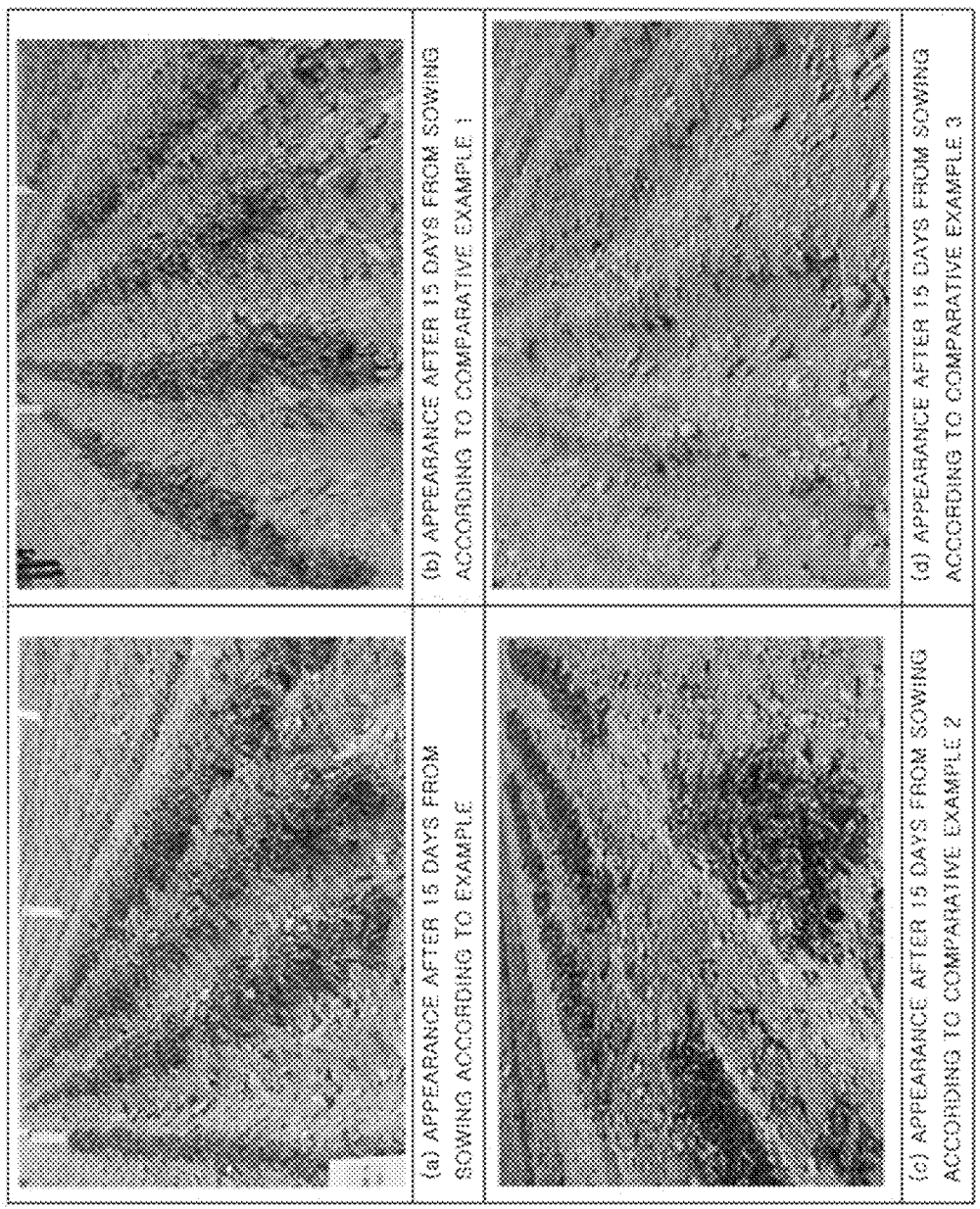
FIG. 2 illustrates pictures showing states in which the in vitro microtuber was directly seeded and then appeared after 15 days according to the example and Comparative Examples 1, 2, 3 of the present invention.

In terms of Comparative Example 2, there was a great loss due to molds that were generated during storage, and this also affected the emergence rate (see (c) of FIG. 2).

In terms of Comparative Example 3, the emergence period was very long (see (d) of FIG. 2). Examples other than Comparative Example 3 (the example, Comparative Examples 1, 2) gone through the germination process, and in the examples other than Comparative Example 3, the emergence period was shortened by about 3 to 5 times compared to that of Comparative Example 3. In this way, it was confirmed that the emergence period affects the yield of the daughter tubers as mentioned above.

As a result, the emergence period was short compared to the comparative examples, and a large amount of seed potatoes could be harvested due to development of appropriate runner. The seed potatoes harvested according to the example also had higher marketability compared to seed potatoes harvested according to the comparative examples (see (a) of FIG. 3).

What is claimed is:

1. A method for directly seeding an in vitro microtuber, the method comprising:
   a) sterilizing a washed in vitro microtuber with chlorine dioxide ($ClO_2$) and drying the sterilized in vitro microtuber;
   b) irradiating the dried in vitro microtuber with light and greening the dried in vitro microtuber;
   c) putting the greened in vitro microtuber in a storage container and storing the greened in vitro microtuber in a temperature range of 2 to 4° C.;
   d) germinating the stored in vitro microtuber; and
   e) seeding the in vitro microtuber,
   wherein step b) is performed for 7 to 10 days under conditions including 3,000 to 4,000 lux of light and 40 to 60% of humidity,
   wherein step b) is a step of irradiating the in vitro microtuber with light for 12 hours and shading the in vitro microtuber from light for 12 hours every day, and
   wherein step d) is performed for 4 weeks under conditions including 3,000 to 4,000 lux of light and 40 to 60% of humidity.

2. The method of claim 1, wherein step d) includes
   step d1) shading the in vitro microtuber from light for 24 hours a day for a week while sequentially changing temperatures;
   step d2) irradiating the in vitro microtuber with light for 7 to 12 hours and shading the in vitro microtuber from light for 12 to 17 hours every day for a week;
   step d3) irradiating the in vitro microtuber with light for 15 to 20 hours and shading the in vitro microtuber from light for 4 to 9 hours every day for a week; and
   step d4) irradiating the in vitro microtuber with light for 20 hours and shading the in vitro microtuber from light for 4 hours every day for a week.

3. The method of claim 2, wherein, during a week in which step d1) is performed, step d1) is performed at 10° C. on a first day, 15° C. on a second day, and in a temperature range of 20 to 25° C. from a third to a seventh day.

4. The method of claim 2, wherein steps d2) to d4) are performed in a temperature range of 20 to 25° C.

* * * * *